United States Patent [19]

Tauscher et al.

[11] 3,946,013

[45] Mar. 23, 1976

[54] 1,3-BIS(BETA-ETHYLHEXYL)-5-AMINO-5-METHYLHEXAHYDROPYRIMIDINE-PYRIDINE-3-CARBOXYLATE, PROCESS FOR ITS PREPARATION AND PHARMACEUTICAL COMPOSITIONS CONTAINING THIS COMPOUND

[75] Inventors: Manfred Tauscher; Joachim Göring, both of Gronau; Wolfgang Busch, Alfeld; Oskar Rohte, Kheden, all of Germany

[73] Assignee: Johann A. Wulfing, Dusseldorf and Neuss, Germany

[22] Filed: Feb. 28, 1974

[21] Appl. No.: 446,925

[30] Foreign Application Priority Data
Mar. 1, 1973 Germany............................ 2310337
Mar. 1, 1973 Germany............................ 2310338

[52] U.S. Cl.......................... 260/256.4 N; 424/251

[51] Int. Cl.$^2$...................................... C07D 239/04
[58] Field of Search............. 260/256.4 N, 256.4 H, 260/256.4 B

[56] References Cited
UNITED STATES PATENTS

| | | | |
|---|---|---|---|
| 3,278,536 | 10/1966 | Elslager et al................ | 260/256.4 B |
| 3,749,721 | 7/1973 | Herrmann et al............ | 260/256.4 H |

*Primary Examiner*—Richard J. Gallagher
*Assistant Examiner*—James H. Turnipseed
*Attorney, Agent, or Firm*—Kenyon & Kenyon

[57] ABSTRACT

1,3-bis($\beta$-ethylhexyl)-5-amino-5-methylhexahydropyrimidine pyridine-3-carboxylate(hexetidine nicotinate), which has greater bacteriostatic activity and lower toxicity in comparison with hexetidine or other salts of hexetidine, is prepared by reacting hexetidine or an acid addition salt thereof with nicotinic acid in an organic solvent.

1 Claim, No Drawings

1,3-BIS(BETA-ETHYLHEXYL)-5-AMINO-5-METHYLHEXAHYDROPYRIMIDINE-PYRIDINE-3-CARBOXYLATE, PROCESS FOR ITS PREPARATION AND PHARMACEUTICAL COMPOSITIONS CONTAINING THIS COMPOUND

The present invention pertains to a novel antibacterial compound, to a process for its preparation and to pharmaceutical compositions containing it. More particularly, this invention is concerned with 1,3-bis($\beta$-ethylhexyl)-5-amino-5-methylhexahydropyrimidine pyridine-3-carboxylate, hereinafter referred to as "hexetidine nicotinate", a process for its preparation and pharmaceutical compositions containing it.

It is known from studies of Witold Saski and S. G. Shah (Journal of Pharmaceutical Science, 54, 277–280 (1965) that 1,3-bis($\beta$-ethylhexyl)-5-amino-5-methyl-hexahydropyrimidine, hereinafter referred to as "hexetidine", has a remarkable antibacterial activity. F. A. Barkley, F. J. Turner, R. S. Pianotti, P. L. Carthage and B. S. Schwartz (in Antimicrobial Agents Annual 507–519 (1960/1961) report that the salt formation of hexetidine with organic acids sometimes enhances this activity.

Surprisingly it was now found that a hitherto unknown salt of hexetidine, namely 1,3-bis($\beta$-ethylhexyl)-5-amino-5-methylhexahydropyrimidine pyridine-3-carboxylate or "hexetidine nicotinate", shows a particularly favorable increase in antibacterial activity and is therefore specially suited as active compound in pharmaceutical compositions. Hexetidine nicotinate is represented by the structural formula:

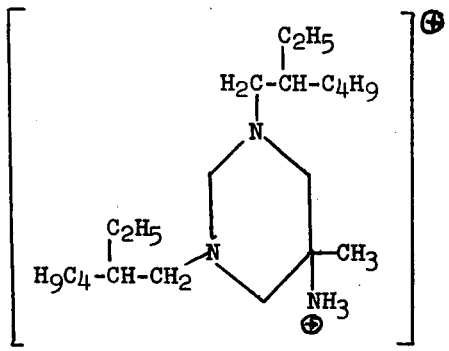
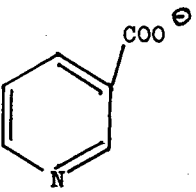

The chemical and physical data of this new compound are as follows:

Elemental analysis: $C_{27}H_{50}N_4O_2$

|  | C | H | N | O |
|---|---|---|---|---|
| Calculated: | 70.08 | 11.15 | 12.10 | 6.92 |
| Found: | 69.31 | 10.78 | 11.92 | 7.87 |

Molecular weight: 462.73
IR spectrum: 3250 cm$^{-1}$ (NH)
1630 cm$^{-1}$ (amide I)

The process of this invention for preparing this new compound relies on the fact that hexetidine nicotinate separates from solutions of hexetidine or its acid addition salts when adding nicotinic acid or a salt thereof.

The process for preparing hexetidine nicotinate is therefore characterized in that a solution of hexetidine or an acid addition salt thereof in an organic solvent is reacted with nicotinic acid or a salt thereof in a molar ratio of about 1 : 1, the reaction mixture is cooled and the precipitated hexetidine nicotinate is recovered. If the hexetidine compound used as the starting material does not have the desired purity this salt formation reaction may also be employed for purifying crude hexetidine.

In the synthesis of hexetidine a number of by-products are formed, totalling about 20 percent by weight. Such compounds mainly comprise $N_1$, $N_3$-bis(ethylhexyl)-2-methyl-1,2,3-propane triamine and 2,6-bis($\beta$-ethylhexyl)-hexahydro-7$\alpha$-methyl-1H-imidazo-(1,5-e)imidazole as well as minor amounts of other impurities. These by-products have to be eliminated because they impair the use of hexetidine in pharmaceutical compositions. Removing these by-products by distillation involves practical difficulties because the most important ones have almost the same boiling point as hexetidine. When separating hexetidine nicotinate in the form of a salt of low solubility from solutions of hexetidine or acid addition salts thereof by adding nicotinic acid or a salt thereof, the undesired by-products, which under these conditions form more readily soluble salts, remain dissolved.

By adding hexetidine nicotinate to an aqueous solution of a base, hexetidine is set free and can be extracted into a water-immiscible organic solvent, the solvent being finally removed from the extract.

The free hexetidine base is obtained by adding hexetidine nicotinate to solutions of, e.g. aliphatic or aromatic amines or alkaline earth hydroxides. Aqueous buffer solutions having a higher basicity may also be used. Preferred bases include 0.1–1N sodium hydroxide, sodium carbonate, 0.1–1N potassium hydroxide and aqueous ammonia. The free hexetidine base is extracted into a water-immiscible solvent. Preferred extraction agents include petroleum ether (40°–80°C), benzene and diethyl ether. In a special embodiment of the invention the solvent is removed under vacuum (5–10 mm Hg) at 40°–50°C, yielding hexetidine of more than 99% purity.

Pure hexetidine obtained in this manner serves as an excellent starting material for preparing the corresponding nicotinic acid salt, especially when using the latter as active compound in pharmaceutical compositions.

Suitable solvents include normally-liquid (i.e. liquid at room temperature), aliphatic, alicyclic and aromatic hydrocarbons, lower aliphatic alcohols having up to 6 carbon atoms or mixtures thereof with water, ketones having up to 6 carbon atoms, aliphatic and alicyclic ethers having up to 8 carbon atoms, acid amides, and sulfoxides. Preferred solvents include petroleum ether (40°–80°C), methanol, n-hexane, dimethyl formamide, isopropanol, benzene, and ethyl alcohol.

The reaction with nicotinic acid or a salt thereof is conveniently carried out at a temperature below the boiling point of the solvent, preferably at a temperature of about 40° to 60°C.

The following examples serve to illustrate the invention, without being construed as limiting the scope of protection.

EXAMPLE 1

Hexetidine (1 mole) was dissolved in 1,000 ml petroleum ether (40°–80°C) and nicotinic acid (1 mole) was added dropwise under stirring at 25°C. The reaction mixture was refluxed for 2 hours and cooled to room temperature under stirring to give a crystal slurry which was filtered under vacuum and dried at 50°–80°C.

Hexetidine nicotinate yield: 60 percent (m.p. 108°–111°C).

EXAMPLE 2

Hexetidine (1 mole) was dissolved in 1,000 ml methanol and heated to 50°C. To the solution nicotinic acid (1 mole) was added dropwise. After stirring for 1.5 hours at 50°C, half of the solvent was distilled off under vacuum at 40°C. The crystal slurry obtained at room temperature was filtered and recrystallized from acetic acid ethyl ester, yielding hexetidine nicotinate as white crystals.

Yield: 70 percent.

EXAMPLE 3

Hexetidine (0.1 mole) was dissolved in 40.0 ml n-hexane and heated to 55°C. Nicotinic acid (0.1 mole) was added under stirring. Hexetidine nicotinate precipitated after cooling to room temperature.

Yield: 70 percent.

EXAMPLE 4

Hexetidine (0.1 mole) was dissolved at 40°C in dimethyl formamide, 0.1 mole nicotinic acid was added and the solution was stirred for 0.5 hours at 40°C. After cooling, hexetidine nicotinate precipitated and was recovered.

Yield: 80 percent.

EXAMPLE 5

Hexetidine (0.1 mole) was dissolved in 30.0 ml isopropanol and heated to 60°C. After addition of 0.1 mole nicotinic acid, the solution was cooled to room temperature under stirring and the resultant crystal slurry of hexetidine nicotinate was filtered under vacuum.

Yield: 60–70 percent.

EXAMPLE 6

Hexetidine (0.1 mole) was dissolved in benzene at 40°C and nicotinic acid was added dropwise. The solution was reacted for 2 hours and cooled under stirring to yield crystals of hexetidine nicotinate which were filtered and dried.

Yield: 60 percent

EXAMPLE 7

Nicotinic acid (0.1 mole) was dissolved in 45.0 ml ethanol and 0.1 mole hexetidine in 10.0 ml ethanol were added dropwise under stirring at 50°C. Stirring was continued at 50°C for 2.5 hours and the solution was then cooled to room temperature. Hexetidine nicotinate precipitated and was separated under vacuum.

Yield: 65–70 percent

EXAMPLE 8

A. To obtain the free base, hexetidine nicotinate prepared from 1 mole crude hexetidine (80% purity) was added to 1,000 ml 1N sodium hydroxide solution. After the addition of petroleum ether (40°–80°C), the mixture was stirred until the salt was completely dissolved. The organic phase was separated, washed with water and dried. The solvent was removed under vacuum (about 5–10 mm Hg) at 40°C.

Pure hexetidine yield: 50–60 percent.

B. To obtain the free base, hexetidine nicotinate prepared from 1 mole crude hexetidine (80% purity) was suspended in an excess of 1N aqueous potassium hydroxide solution, then 1,000 ml benzene were added. After the salt was completely dissolved the organic phase was separated, washed with water and dried over sodium sulfate. The solvent was removed under vacuum (5–10 mm Hg) at 50°C.

Pure hexetidine yield: 60–70 percent.

C. Hexetidine nicotinate obtained from 1 mole crude hexetidine (80% purity) was mixed with an excess of 3% ammonia solution. The free hexetidine base was taken up in 50.0 ml diethyl ether. The organic phase was separated, washed with water and dried over sodium sulfate. The solvent was removed under vacuum (5–10 mm Hg) at 50°C.

Pure hexetidine yield: 70 percent.

D. Hexetidine nicotinate obtained from 1 mole crude hexetidine (80% purity) was mixed with an excess of 1N sodium hydroxide solution and the free base was taken up in 60.0 ml petroleum ether (40°–80°C). The organic phase was dried over sodium sulfate and the solvent was removed under vacuum (5–10 mm Hg) at 50°C.

Pure hexetidine yield: 80 percent.

E. Hexetidine nicotinate obtained from 1 mole crude hexetidine (80% purity) was treated with an excess of 5% aqueous sodium carbonate solution and taken up in petroleum ether (40°–80°C). The organic phase was separated and dried. The solvent was removed under vacuum (5–10 mm Hg) at 50°C.

Pure hexetidine yield: about 60 percent.

F. Hexetidine nicotinate obtained from 1 mole crude hexetidine (80% purity) was mixed with 1N potassium hydroxide solution. After the addition of 40.0 ml diethyl ether, the solution was stirred until the salt was completely dissolved. The organic phase was dried over sodium sulfate and the extracting agent removed under vacuum (5–10 mm Hg) at 40°C.

Pure hexetidine yield: 60 percent.

G. Hexetidine nicotinate obtained from 1 mole crude hexetidine (80% purity) was mixed with an excess of 3% ammonia solution. The free hexetidine was taken up in 40.0 ml petroleum ether. The extracting agent was removed under vacuum (5–10 mm Hg) at 40°C.

Pure hexetidine yield: 65 percent.

The purity of hexetidine obtained in (A) to (G) is 99.92 to 99.98 percent. Index of refraction of the pure product: $[n]_D^{20} = 1.4652$.

Reaction of pure hexetidine with nicotinic acid or a salt thereof according to examples 1 to 7 gives the desired hexetidine nicotinate in high yields.

TOXICITY AND BACTERIOSTATIC ACTIVITY

When subjecting hexetidine, hexetidine oxalate, hexetidine cinnamate and hexetidine nicotinate to toxicological and microbiological comparative tests, hexetidine nicotinate was found to have particularly favorable properties. Thus the toxicity of hexetidine was substantially reduced by the salt formation reaction with nicotinic acid. Female NMRI mice having a body weight of 20–30 g were used as test animals. The observation period was 10 days. The hexetidine salts were suspended in commercial carboxymethyl cellulose and 10 ml/kg of the suspension were injected. The results were determined by the method of Litchfield and Wilcoxon (G. T. Litchfield and F. G. Wilcoxon in Pharmacol. exp. Therap. 96, 99 (1949)).

The following $LD_{50}$ values were obtained:

| Test Compound | Toxicity, $LD_{50}$ | |
|---|---|---|
| | p.o. (mg/kg) | i.p. (mg/kg) |
| Hexetidine | 960 (519 – 1,776) | 33 (20 – 55) |
| Hexetidine oxalate | 970 (561 – 1,678) | 23 (19 – 29) |
| Hexetidine cinnamate | 1,740 (1,543 – 1,963) | 54 (35 – 83) |
| Hexetidine nicotinate | 1,830 (1,331 – 2,516) | 63 (46 – 86) |

For a determination of bacteriostatic activity, solutions of hexetidine, hexetidine oxalate and hexetidine nicotinate having the following compositions were compared:

| | |
|---|---|
| Hexetidine solution | 100 mg hexetidine per 100 ml |
| Hexetidine oxalate solution | 113.2 mg hexetidine oxalate (corresponding to 100 mg hexetidine) per 100 ml |
| Hexetidine nicotinate solution | 136.2 mg hexetidine nicotinate (corresponding to 100 mg hexetidine) per 100 ml |

The inoculum suspension was obtained by inoculation of a sterile Petri dish containing nutrient agar (standard I) with a test culture of bacterial parent strains (Escherichia coli, Proteus vulgaris, Pseudomonas aeruginosa) and incubation at 30°C for 24 hours. The suspension was either used immediately or stored at +4°C. The organisms grown in the Petri dish were elutriated with 5 ml physiological brine solution and diluted 1:10 with the same solution to a volume of 50 ml. Then 250 ml double concentrated thioglycolate solution (60 g/l) were mixed with 100 drops (about 5 ml) of the above 1:10 diluted primary culture of bacterial parent strains and shaken to obtain a uniform suspension. Serial dilutions were prepared for each of the above-mentioned compound solutions in the following concentrations, each comprising 10 test tubes of 100 ml:

hexetidine per ml: 1,000; 500; 250; 125; 62.5; about 31; about 16; about 8; about 4; about 2.

Next, 5 ml double concentrated thioglycolate nutrient solution inoculated with the test organisms were added to each test tube by means of a pipet. Each test tube thus contained 50% of the final concentration. The results were determined after incubation of the serial dilutions at 30°C for 24 to 72 hours. Complete absence of cloudiness (growth) in a test tube after 72 hours incubation indicates the minimum inhibitory concentration (MIC).

The table shows the bacteriostatic activity in relation to concentration:

| Solution | Hexetidine contained in 100 mg solution | Bacteriostatic activity after | | | | | |
|---|---|---|---|---|---|---|---|
| | | 1 | 2 | 3 | 4 | 5 | 6 days |
| Hexetidine | 100 mg | | | | | 125γ | |
| Hexetidine oxalate | 100 mg | 500γ | | | | | |
| Hexetidine nicotinate | 100 mg | | | | | | 62.5γ |

All samples were incubated at 30°C for 6 days.

After 6 days hexetidine still showed a satisfactory activity at a concentration of 125γ. Hexetidine oxalate showed no significant activity at a concentration of as high as 500γ, whereas hexetidine cinnamate could not be tested due to extreme insolubility. Hexetidine nicotinate still showed an activity at a concentration of 62.5γ.

What is claimed is:

1. 1,3-Bis (β-ethylhexyl)-5-amino-5-methylhexahydropyrimidinepyridine-3-carboxylate.

* * * * *